(12) United States Patent
Rubin et al.

(10) Patent No.: US 7,872,042 B2
(45) Date of Patent: Jan. 18, 2011

(54) **USE OF TOCOTRIENOLS FOR ELEVATING *IKBKAP* GENE EXPRESSION AND TREATING FAMILIAL DYSAUTONOMIA**

(76) Inventors: Berish Y. Rubin, 6 Krashes Ct., Monsey, NY (US) 10952; Sylvia L. Anderson, 179 Broadway, Cresskill, NJ (US) 07626

( * ) Notice: Subject to any disclaimer, the term of this patent is extended or adjusted under 35 U.S.C. 154(b) by 1467 days.

(21) Appl. No.: 11/128,492

(22) Filed: May 13, 2005

(65) Prior Publication Data
US 2005/0288362 A1    Dec. 29, 2005

Related U.S. Application Data

(60) Provisional application No. 60/571,367, filed on May 14, 2004.

(51) Int. Cl.
  *A01N 43/16*  (2006.01)
  *A61K 31/35*  (2006.01)
  *A61K 31/355* (2006.01)
  *C07D 311/00* (2006.01)

(52) U.S. Cl. .................. 514/456; 514/458; 549/398; 549/406

(58) Field of Classification Search .......... 514/458, 514/456; 536/23.1; 549/398, 406
See application file for complete search history.

(56) References Cited

FOREIGN PATENT DOCUMENTS

| WO | WO 96/19218   | * | 6/1996  |
|----|---------------|---|---------|
| WO | WO 00/78296   | * | 12/2000 |
| WO | WO 2005/009135| * | 2/2005  |

OTHER PUBLICATIONS

Nesaretnam et al Abstract Lipids 1998 33 461.*
Chatelain et. al., Biochimica et Biophysica Acta, 1993, Elsevier Science Ltd., vol. 1176, pp. 83-89.*

* cited by examiner

*Primary Examiner*—Sreeni Padmanabhan
*Assistant Examiner*—Sarah Pihonak
(74) *Attorney, Agent, or Firm*—Scully, Scott, Murphy & Presser, P.C.

(57) ABSTRACT

The present invention provides methods for elevating IKBKAP gene expression and the level of functional IKAP protein in cells, which are beneficial to human individual, such as an individual suffering from Familial Dysautonomia, by providing one or more tocotrienols alone or in combination with one or more tocopherols to the cells. The present invention also provides methods for treating Familial Dysautonomia by providing tocotrienols alone or in combination with one or more tocopherols to a patient having Familial Dysautonomia. Related therapeutic kits are also provided.

8 Claims, 9 Drawing Sheets

SEQUENCE LISTING

```
<160> NUMBER OF SEQ ID NOS: 6

<210> SEQ ID NO 1
<211> LENGTH: 18
<212> TYPE: DNA
<213> ORGANISM: artificial sequence
<220> FEATURE:
<223> OTHER INFORMATION: oligonucleotide primer

<400> SEQUENCE: 1
agttgttcat catcgagc                                                 18

<210> SEQ ID NO 2
<211> LENGTH: 23
<212> TYPE: DNA
<213> ORGANISM: artificial sequence
<220> FEATURE:
<223> OTHER INFORMATION: oligonucleotide primer
```

-continued

```
<400> SEQUENCE: 2
catttccaag aaacacctta ggg                                              23

<210> SEQ ID NO 3
<211> LENGTH: 28
<212> TYPE: DNA
<213> ORGANISM: artificial sequence
<220> FEATURE:
<223> OTHER INFORMATION: oligonucleotide primer

<400> SEQUENCE: 3
caggacacaa agcttgtatt acagactt                                         28

<210> SEQ ID NO 4
<211> LENGTH: 23
<212> TYPE: DNA
<213> ORGANISM: artificial sequence
<220> FEATURE:
<223> OTHER INFORMATION: oligonucleotide primer

<400> SEQUENCE: 4
catttccaag aaacacctta ggg                                              23

<210> SEQ ID NO 5
<211> LENGTH: 19
<212> TYPE: DNA
<213> ORGANISM: artificial sequence
<220> FEATURE:
<223> OTHER INFORMATION: oligonucleotide primer

<400> SEQUENCE: 5
gagatcatcc aagaatcgc                                                   19

<210> SEQ ID NO 6
<211> LENGTH: 18
<212> TYPE: DNA
<213> ORGANISM: artificial sequence
<220> FEATURE:
<223> OTHER INFORMATION: oligonucleotide primer

<400> SEQUENCE: 6
ggtagctgaa ttctgctg                                                    18
```

USE OF TOCOTRIENOLS FOR ELEVATING *IKBKAP* GENE EXPRESSION AND TREATING FAMILIAL DYSAUTONOMIA

CROSS REFERENCED TO RELATED APPLICATIONS

The present application claims benefit of U.S. Provisional Application No. 60/571,367 filed May 14, 2004.

FIELD OF THE INVENTION

The present invention relates to the use of tocotrienols for elevating IKBKAP gene expression and the level of functional IKAP protein, which is beneficial to individuals suffering from Familial Dysautonomia as well as normal individuals. The present invention also relates to methods and kits for treating Familial Dysautonomia.

BACKGROUND OF THE INVENTION

Familial Dysautonomia (FD), also known as "Riley-Day Syndrome" or "hereditary sensory neuropathy type III" (MIM 223900), is an autosomal recessive disorder primarily confined to individuals of Ashkenazi Jewish descent. FD affects the development and survival of sensory, sympathetic, and some parasympathetic neurons (C. M. Riley, et al., "Central Autonomic Dysfunction with Defective Lacrimation", *Pediatrics* 3: 468-477 (1949); F. B. Axelrod, et al., Familial Dysautonomia: Diagnosis, Pathogenesis and Management, *Adv. Pediatr.* 21: 75-96 (1974); F. B. Axelrod, et al., "Familial Dysautonomia", in: D. Robertson, P. A. Low, R. J. Polinsky (Eds.), *Primer on the Autonomic Nervous System*, Academic Press, San Diego, pp. 242-249 (1996)) and is caused by mutations in the gene termed IKBKAP which encodes a protein termed IKAP (IκB kinase complex-associated protein) (S. L. Anderson, et al., "Familial Dysautonomia Is Caused by Mutations of the IKAP Gene", *Am. J. Hum. Genet.* 68: 753-758 (2001); S. A. Slaugenhaupt, et al., "Tissue-Specific Expression of a Splicing Mutation in the IKBKAP Gene Causes Familial Dysautonomia", *Am. J. Hum. Genet.* 68: 598-605 (2001)). IKAP was initially reported to be a scaffold protein involved in the assembly of the IκB kinase complex (L. Cohen, et al., "IKAP is a Scaffold Protein of the IkB Kinase Complex", *Nature* 395: 292-297 (1998)), but subsequently was reported to have no association with this complex (D. Krappmann, et al., "The IkB Kinase (IKK) Complex is Tripartite and Contains IKKγ but not IKAP as a Regular Component", *J. Biol. Chem.* 275: 29779-29787 (2000)). IKAP is homologous to the Elp1 protein of the *Saccharomyces cerevisiae* Elongator complex (G. Otero, et al., "Elongator, a Multisubunit Component of a Novel RNA Polymerase II Holoenzyme for Transcriptional Elongation", *Mol. Cell* 3: 109-118 (1999)) and is a component of the human Elongator complex (N. A. Hawkes, et al., "Purification and Characterization of the Human Elongator Complex, *J. Biol. Chem.* 277: 3047-3052 (2002)). IKAP has recently been reported to be a c-Jun N-terminal kinase (JNK)-associated protein capable of JNK stress kinase activation (C. Holmberg, et al., "A Novel Specific Role for 1 Kappa B Kinase Complex-Associated Protein in Cytosolic Stress Signaling", *J. Biol. Chem.* 277: 31918-31928 (2002)). The multiple biological activities of IKAP and their roles in FD-mediated neurological deficits remain to be elucidated.

Two FD-causing mutations have been identified in individuals of Ashkenazi Jewish descent. The more common, or major, FD-causing mutation occurs in the donor splice site of intron 20, resulting in aberrant splicing that produces an IKAP transcript lacking exon 20. Translation of this mRNA results in a frameshift that generates a truncated protein lacking all of the amino acids encoded in exons 20-37. The less common, or minor, mutation is a G→C transversion that results in an arginine to proline substitution of amino acid residue 696 of IKAP (S. L. Anderson, et al., "Familial Dysautonomia Is Caused by Mutations of the IKAP Gene", *Am. J. Hum. Genet.* 68: 753-758 (2001); S. A. Slaugenhaupt, et al., "Tissue-Specific Expression of a Splicing Mutation in the IKBKAP Gene Causes Familial Dysautonomia", *Am. J. Hum. Genet.* 68: 598-605 (2001)).

Mutations that affect RNA splicing are a major cause of human genetic diseases. These diseases may occur as a result of mutations in the splice donor or splice acceptorsequences or in exons or introns, generating cryptic splice junctions. While many of these mutations result in what appears to be an absolute absence of the appropriately spliced gene product, in some cases mutations that affect splicing result in a milder form, or an adult onset form, of the disease in which "leaky" alternative mRNA splicing is observed that produces both mutant (skipped exon) and wild-type (full-length) transcripts (M. L. Huie, et al., "Glycogen Storage Disease Type II: Identification of Four Novel Missense Mutations (D645N, G648S, R672W, R672Q) and Two Insertions/Deletions in the Acid Alpha-Glucosidase Locus of Patients of Differing Phenotype", *Biochem. Biophys. Res. Commun.* 244: 921-927 (1998); C. F. Boerkoel, et al., "Leaky Splicing Mutation in the Acid Maltase Gene is Associated with Delayed Onset of Glycogenosis Type II, *Am. J. Hum. Genet.* 56: 887-897 (1995); S. Beck, et al., "Cystic Fibrosis Patients with the 3272-26A→G Mutation Have Mild Disease, Leaky Alternative mRNA Splicing, and CFTR Protein at the Cell Membrane", *Hum. Mutat.* 14: 133-144 (1999); S. Kure, et al., "Glycogen Storage Disease Type Ib Without Neutropenia", *J. Pediatr.* 137: 253-256 (2000); I. K. Svenson, et al., "A Second Leaky Splice-Site Mutation in the Spastin Gene", *Am. J. Hum. Genet.* 69: 1407-1409 (2001); I. K. Svenson, et al., "Identification and Expression Analysis of Spastin Gene Mutations in Hereditary Spastic Paraplegia", *Am. J. Hum. Genet.* 68: 1077-1085 (2001)). The major FD-causing mutation, termed 2507+6T→C or IVS20$^{+6T \to C}$, changes the sequence of the splice donor element of intron 20 from the consensus GTAAGT to a non-consensus GTAAGC, resulting in the generation of a transcript lacking exon 20. This mutation appears to be somewhat leaky as both the mutant and wild-type transcripts are detected in lymphoblasts of individuals homozygous for this FD-causing mutation (S. A. Slaugenhaupt, et al., "Tissue-Specific Expression of a Splicing Mutation in the IKBKAP Gene Causes Familial Dysautonomia", *Am. J. Hum. Genet.* 68: 598-605 (2001)).

As FD-derived cells produce the full-length IKAP transcript, it is a goal of the present invention to identify agents that either promote splicing that generates the exon 20-containing transcript or up-regulate IKAP transcription which, due to the somewhat leaky nature of this mutation, could generate increased levels of the correctly spliced transcript and, thereby, more functional IKAP protein in order to treat FD.

SUMMARY OF THE INVENTION

It has been found in work leading to the present invention that tocotrienols, members of the vitamin E family, have the ability to increase transcription of IKAP mRNA in FD-derived cells, with corresponding increases in the correctly spliced IKAP transcript and normal IKAP. It has also been found that tocotrienols have the ability to increase transcription of IKAP mRNA in cells derived from normal individuals.

Accordingly, in one embodiment, the present invention provides a method for elevating the level of the IKBKAP gene expression in a cell by bringing the cell into contact with an effective amount of a tocotrienol, such as α, β, γ or δ tocotrienol, or a combination thereof.

In another embodiment, the present invention provides a method of elevating the level of the IKAP protein in a cell by bringing the cell into contact with an effective amount of one or more tocotrienols.

In still another embodiment, the cells are contacted with an effective amount of one or more tocotrienols in combination with one or more tocopherols to achieve an elevated level of the IKBKAP gene expression or the IKAP protein. According to the present invention, a tocopherol can enhance a tocotrienol-induced elevation of IKAP mRNA levels, even though the tocopherol alone does not have an impact on IKAP mRNA levels.

In another embodiment, the present invention provides a method for treating an FD patient by providing an effective amount of one or more tocotrienols to the patient, preferably through an oral route.

In still another embodiment, an FD patient is treated by providing an effective amount of one or more tocotrienols in combination with one or more tocopherols.

In a further embodiment, the present invention provides a kit for treating an FD patient. The kit contains an effective amount of one or more tocotrienols alone or in combination with one or more tocopherols and instructions that typically set forth suitable dosages and dosing schedules effective for treatment of FD. The kit can also include a pharmaceutically acceptable carrier.

BRIEF DESCRIPTION OF THE DRAWINGS

FIG. 2. Real-time RT-PCR analysis of the IKAP RNA. cDNA was generated from FD-derived human fibroblast (GM00850) cells incubated for 48 h in the presence of varying concentrations of δ-tocotrienol. Real-time RT-PCR analysis was performed to measure the relative amounts of the IKAP RNAs produced by these cells. Results, the mean of three experiments, each done in triplicate, were expressed as changes in the threshold cycle ($\Delta C_T$) relative to results from untreated cells.

FIG. 4. Nuclear run-on transcriptional analysis of the IKAP RNA in response to δ-tocotrienol treatment. Radiolabeled RNA was purified from nuclei prepared from GM04663 cells incubated for 48 h in the presence or absence of 12.5 µg/ml of δ-tocotrienol. The RNA was hybridized for 48 h to a membrane to which cDNAs for IKAP and GAPDH were spotted and crosslinked. The relative amount of radioactivity associated with the cDNA was determined densitometrically and is expressed as a percentage of the signal generated in the untreated cells. The experiment depicted was a typical result obtained.

FIG. 5. The induction of full-length IKAP in FD-derived (GM00850 and GM04663) and normal (GM02912) cells. Lysates prepared from cells incubated in the presence or absence of 12.5 µg/ml of δ-tocotrienol for 48 h were fractionated and characterized by Western blot analysis. The presence of IKAP was detected using a monoclonal antibody recognizing a fragment of the IKAP protein encoded by exons 25-28 of IKBKAP. Relative amounts of IKAP produced were determined densitometrically. Values expressed are as a percentage of the IKAP levels present in the untreated normal (GM02912) cells. Following immunological screening, the blot was stained with Coomassie brilliant blue to confirm that equal amounts of protein were loaded on the gel. The Western blot presented is representative of the experiments performed.

DETAILED DESCRIPTION OF THE INVENTION

Familial Dysautonomia (FD) is a neurodegenerative genetic disorder primarily affecting individuals of Ashkenazi Jewish descent and is caused by mutations in the IKBKAP gene that encodes the Iκ-B kinase complex-associated protein (IKAP). The major mutation causes aberrant splicing, resulting in the production of a truncated form of IKAP. Tissues from individuals homozygous for the major mutation contain both mutant and wild-type IKAP transcripts.

The present inventors have discovered that tocotrienols, members of the vitamin E family, have the ability to increase transcription of IKAP mRNA in FD-derived cells, with corresponding increases in the correctly spliced IKAP transcript and normal IKAP protein. Furthermore, tocotrienols have been found to increase normal IKAP mRNA levels in blood from individuals with FD. In addition, tocotrienols have been found to increase transcription of IKAP mRNA in cells derived from normal individuals, i.e., individuals without FD. Accordingly, the present invention provides therapeutic methods employing tocotrienols.

More specifically, in one embodiment, the present invention provides a method for elevating the level of the IKBKAP gene expression in a cell by bringing the cell into contact with an effective amount of one or more tocotrienols.

By "cell" is meant to include cells derived from an individual or cells within an individual. The individual can be an individual with FD or a normal individual.

By "bringing the cell into contact with an effective amount of a tocotrienol" is meant to include contacting the cell in vitro with the tocotrienol, as well as providing or administering the tocotrienol to an individual such that the cell is exposed to the tocotrienol in vivo in the individual.

Tocotrienols are well known members of the Vitamin E family and are generally characterized by the following structure formula (I):

(I)

wherein R1 and R2 are hydrogen or lower alkyl, such as methyl, ethyl, or n-propyl, which is unsubstituted or substituted by halogen or hydroxyl, for example.

According to the present invention, preferred tocotrienols for use in the present methods include α, β, γ and δ tocotrienols, wherein R1 and R2 are as follows:

| $R^1$ | $R^2$ | |
|-------|-------|---|
| $CH_3$ | $CH_3$ | α-Tocotrienol |
| $CH_3$ | H | β-Tocotrienol |
| H | $CH_3$ | γ-Tocotrienol |
| H | H | δ-Tocotrienol |

It should be recognized that tocotrienols suitable for use in the present invention are not limited to α, β, γ and δ tocotrienols, and include compounds having the structure formula (I) with substituents (such as halogen, hydroxyl or lower alkyl) on the aromatic ring different from those in α, β, γ and δ tocotrienols.

Tocotrienols can be readily obtained from various commercial sources, such as Twin Laboratories, Inc. (American Fork, Utah).

According to the present invention, tocotrienols can be employed individually (i.e., a single type of tocotrienol compound) or in combination (i.e., two or more tocotrienol compounds).

The amount of a tocotrienol that is effective may vary, depending on the manner by which the cell is brought into contact with the tocotrienol. In general, a suitable dose of tocotrienol in the range of 1 to 1000 mg per day is effective to elevate the level of the IKBKAP gene expression in cells in vivo within an individual. Preferably, an amount in the range of 50 to 200 mg per day is provided to an individual. When cells are exposed to tocotrienols in vitro, an amount of tocotrienols in the range of 0.25 to 50 μg/ml, preferably, 10-15 μg/ml, is effective.

The level of the IKBKAP gene expression can be determined by using a variety of methods well known to those skilled in the art, including Northern Blot analysis, RT-PCR, among others. An elevated level of the IKBKAP gene expression in cells treated with tocotrienols is observed when compared with untreated cells.

The elevated level of the IKBKAP gene expression can result in an elevated level of the IKAP protein. Accordingly, in another embodiment, the present invention provides a method of elevating the level of the IKAP protein in a cell by bringing the cell into contact with an effective amount of one or more tocotrienols.

The term "IKBKAP" has been used herein to refer to the gene, whereas "IKAP" has been used to refer to the mRNA transcript or the encoded protein.

The level of the IKAP protein produced in a cell can be determined by using a variety of methods well known to those skilled in the art, including Western Blot analysis. An elevated level of the IKAP protein in cells treated with one or more tocotrienols is observed when compared with untreated cells.

In another embodiment, the cells are contacted with an effective amount of one or more tocotrienols in combination with one or more tocopherols to achieve an elevated level of the IKBKAP gene expression or the IKAP protein produced. According to the present invention, a tocopherol can enhance a tocotrienol-induced elevation of IKAP mRNA levels, even though the tocopherol alone does not have an impact on IKAP mRNA levels.

The term "in combination" does not require simultaneous administration of tocopherols and tocotrienols, so long as both tocopherols and tocotrienols are given to the cell or the individual.

Tocopherols are also members of the Vitamin E family and are generally characterized by the following structure formula (II):

(II)

wherein R1 and R2 are hydrogen or lower alkyl, such as methyl, ethyl, or n-propyl, which is unsubstituted or substituted by halogen or hydroxyl, for example.

According to the present invention, preferred tocopherols for use in the present methods include α, β, γ and δ tocopherols, wherein R1 and R2 are as follows:

| $R^1$ | $R^2$ | |
|-------|-------|---|
| $CH_3$ | $CH_3$ | α-Tocopherol |
| $CH_3$ | H | β-Tocopherol |
| H | $CH_3$ | γ-Tocopherol |
| H | H | δ-Tocopherol |

It should be recognized that tocopherols suitable for use in the present invention are not limited to α, β, γ and δ tocopherols, and include isomers of α, β, γ and δ tocopherols, as well as compounds having the structure formula (II) with substituents (such as halogen, hydroxyl or lower alkyl) on the aromatic ring different from those in α, β, γ and δ tocopherols.

Tocopherols can be readily obtained from various commercial sources, such as Twin Laboratories, Inc. (American Fork, Utah).

The amount of a tocopherol that is effective to potentiate an tocotrienol-induced elevation of IKBKAP gene expression may vary. In general, a suitable dose of tocopherol in the range of 1 to 1000 mg per day is effective to elevate the level of the IKBKAP gene expression in cells in vivo within an individual. Preferably, an amount in the range of 50 to 200 mg per day is provided to an individual. When cells are exposed to tocopherols in vitro, an amount of tocopherols in the range of 0.25 to 50 µg/ml, preferably, 10-15 µg/ml, is effective.

In another embodiment, the present invention provides a method for treating an FD patient by providing an effective amount of one or more tocotrienols to the patient.

The term "treating" is meant to ameliorate, inhibit or eliminate the symptoms associated with FD, or to improve the health of an FD patient. Symptoms known to be associated with FD as a result of the malfunctioning of the autonomic system (such as the blood pressure control system) include hypertensive crisis, lack of sensitivity to pain, wretching, and a lack of overflow tears, among others.

Without intending to be bound by any particular theory, it is believed that supplementation with tocotrienols elevates the level of the IKBKAP gene expression in FD individuals, resulting in increases in the levels of correctly spliced IKAP transcript and normal IKAP protein in the FD individuals, which in turn act directly or indirectly in the treatment of FD.

In accordance with the present invention, tocotrienols can be provided to an FD individual as young as a few weeks old. Tocotrienols are provided to an FD individual throughout their lifetime, from birth, or even prenatally via the mother's ingestion.

Tocotrienols that are effective for use in the present therapeutic methods include, but are not limited to, α, β, γ and δ tocotrienols. These tocotrienols can be given to an FD patient individually or in combination.

The amount of a tocotrienol that is effective may depend on the age, condition and body weight of a particular FD patient. In general, a suitable dose of a tocotrienol in the range of 1 to 1000 mg per day is effective. Preferably, an amount in the range of 50 to 200 mg per day is provided to an FD patient. Tocotrienols can be provided to an FD individual for as long as necessary to treat FD. The duration of treatment can be determined by the skilled artisan without undue experimentation.

Further according to the present invention, tocotrienols can be given to an FD individual alone or in combination with one or more one or more tocopherols. Preferred tocopherols for use in the present methods include, but are not limited to, α, β, γ and δ tocopherols.

The amount of a tocopherol that is effective may depend on the age, condition and body weight of a particular FD patient. In general, a suitable dose of a tocopherol in the range of 1 to 1000 mg per day is effective for use in combination with one or more tocotrienols. Preferably, an amount in the range of 50 to 200 mg of a tocopherol per day is provided to an FD patient in combination with one or more tocotrienols.

Tocotrienols alone or in combination with tocopherols can be provided in a pharmaceutical carrier for use in the present methods. As used herein, a pharmaceutically acceptable carrier includes any and all solvents, dispersion media, isotonic agents and the like. Except insofar as any conventional media, agent, diluent or carrier is detrimental to the recipient or to the therapeutic effectiveness of the active ingredients contained therein, its use in practicing the methods of the present invention is appropriate. The carrier can be liquid, semi-solid, e.g. pastes, or solid carriers. Examples of carriers include water, saline solutions, alcohol, oils, sugar, gel, lipids, liposomes, resins, porous matrices, binders, fillers, coatings, preservatives and the like, or combinations thereof. Carriers that are capable of controlled release, e.g., a controlled release matrix, are also contemplated by the present invention.

In accordance with the present invention, tocotrienols and tocopherols can be combined with a pharmaceutical carrier in any convenient and practical manner, e.g., by admixture, solution, suspension, emulsification, encapsulation, absorption and the like, and can be made in formulations such as tablets, capsules, powder, syrup, suspensions that are suitable for injections, implantations, inhalations, ingestions or the like.

According to the present invention, tocotrienols and tocopherols can be provided to an FD individual by standard routes, including the oral, enteral and parenteral routes. Preferably, an FD individual takes tocotrienols and tocopherols by oral ingestion.

In a further embodiment, the present invention provides a kit for treating an FD patient, which contains an effective amount of tocotrienols alone or in combination with one or more tocopherols and instructions that typically set forth suitable dosages and dosing schedules effective for treatment of FD. The kit can also include a pharmaceutical acceptable carrier that is described hereinabove.

The present invention is further illustrated by the following examples.

EXAMPLE 1

Detection of the Wild Type IKAP Transcript in FD-Derived Tissues

RNA was isolated from a variety of tissues of FD-affected individuals to determine the presence of wild-type IKAP transcript. Frozen tissue was homogenized with a Tissue Tearor (Biospec Products) in Lysis/Binding Solution (Ambion) and the RNA was purified using the RNAqueous Total RNA Isolation Kit (Ambion). The RNA was amplified using a primer recognizing the sequence encoded in exon 20 of the IKBKAP gene and a primer that spans exons 21 and 22 by following the instruction of the GeneAmp EZ rTth RNA PCR Kit (Applied Biosystems). Twenty-five nanograms of RNA were used as template in a reaction volume of 20 µl. One-step RT-PCR was carried out as follows: one cycle of 58° C. for 45 min and 94° C. for 2 min, followed by 45 cycles of 94° C. for 30 s, 58° C. for 30 s, and 72° C. for 30s, and then a final extension of 72° C. for 7 min. PCR products were then analyzed on a 2% agarose gel.

Figure 1:
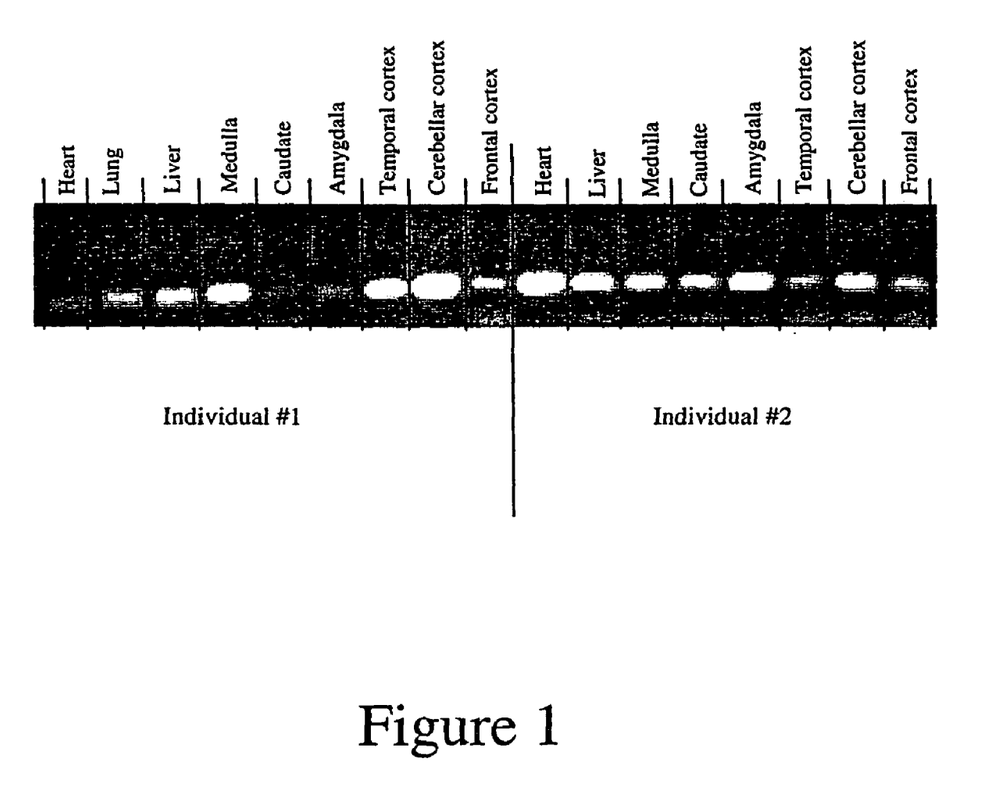
FIG. 1. Expression of IKAP RNA in post-mortem tissue samples. RT-PCR, using primers located in exon 20 and spanning exons 21 and 22, was performed on RNA isolated from post-mortem tissue samples from two individuals with FD. The resulting amplified products were fractionated on a 2% agarose gel.

As shown in FIG. 1, exon 20-containing IKAP transcript was detected in all of the FD-derived tissues studied. This observation is consistent with a recent report by Cuajungco et al. ("Tissue-Specific Reduction in Splicing Efficiency of IKBKAP Due to the Major Mutation Associated with Familial Dysautonomia", *Am. J. Hum. Genet.* 72: 749-758 (2003)).

EXAMPLE 2

δ-Tocotrienol Elevated the Level of IKAP Transcripts

In order to identify agents that could modulate the level of the wild type IKAP transcript produced in FD-derived cells, either by increasing transcription or modulating splicing, FD-derived fibroblast cells (GM00850) were treated with a variety of biological agents. RNA was isolated from the treated cells and was subjected to real-time RT-PCR analysis using primers specific for the wild-type IKAP transcript. More specifically, FD-derived fibroblast cells, seeded in 96-well plates at a concentration of 4000 cells/well for at least one day prior to treatment, were treated in triplicate for approximately 48 h unless noted otherwise. After treatment, the cells were washed once with PBS and then lysed in 50 µl of Cell-to-cDNA lysis buffer (Ambion) at 75° C. for 12 min. After one freeze-thaw cycle, 4 µl of lysate was used in 20 µl RT-PCRs. The Quantitect SYBR Green RT-PCR Kit (Qiagen) was used for real-time RT-PCR analysis of the relative quantities of the exon 20-containing transcript (wild-type), the exon 20-lacking transcript (mutant), as well as an exon 34-35-containing transcript that is unaffected by the FD-causing mutation (total). An ABI PRISM 7000 Sequence Detection System (Applied Biosystems), programmed as follows, was used to perform the real-time RT-PCR and analysis: 50° C. for 30 min and 95° C. for 15 min for one cycle, followed by 40 cycles of 94° C. for 15s, 57-60° C. for 30 s, and 72° C. for 30 s. Primers, used at a concentration of 0.5 µM, are shown in Table 1. To present relative amounts of PCR product obtained, results were expressed as changes in the threshold cycle (ACT) compared to untreated cells. The threshold cycle refers to the PCR cycle at which the fluorescence of the PCR is increased to a calculated level above background. A change of 1.0 in $C_T$, assuming 100% PCR efficiency, would reflect a twofold change in the starting amount of the RNA template that was amplified.

and wild-type transcripts were elevated in a concentration-dependent manner (FIG. 2), with as much as a sixfold increase ($\Delta C_T$=2.5) in the experiment shown, at the highest concentration tested, demonstrating a tocotrienol-mediated increase in the cellular level of the IKAP-encoding RNAs.

Figure 3:
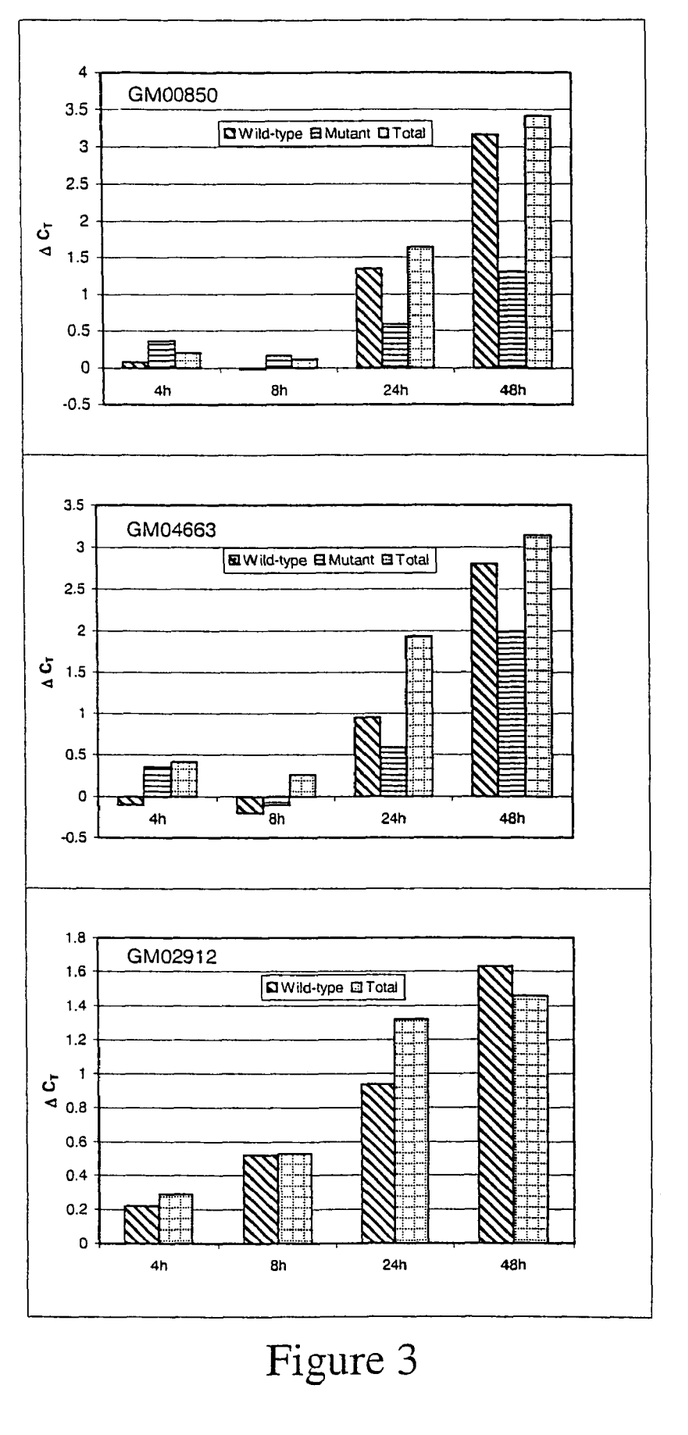
FIG. 3. Time kinetics of the δ-tocotrienol mediated accumulation of the IKAP RNAs. Cultures of FD-derived (GM00850 and GM04663) and normal (GM02912) fibroblast cells were treated for varying times with 12.5 µg/ml of δ-tocotrienol. The relative amounts of the IKAP RNAs were determined by real-time RT-PCR. The results presented represent mean values obtained in three experiments, each done in triplicate.

To characterize the kinetics of the δ-tocotrienol-mediated accumulation of the IKAP transcript, FD-derived (GM00850 and GM04663) and normal (GM02912) fibroblast cells were exposed to 12.5 µg/ml of δ-tocotrienol for periods up to 48 h and the amount of the IKAP-encoding transcripts was determined by real-time RT-PCR, as described above. As can be seen in FIG. 3, significantly elevated levels of these transcripts are detected 24 h following the start of δ-tocotrienol treatment, as compared to untreated cells, and continue to accumulate through 48 h of treatment.

The δ-tocotrienol-mediated accumulation of the IKAP-encoding transcripts was either the result of an elevation in the level of gene transcription or the stabilization of this RNA. To distinguish between these possibilities, nuclear run-on transcription assays were performed on cells incubated in either the presence or absence of δ-tocotrienol. Isolation of nuclei and transcription in the presence of [$\alpha$-$^{32}$P]UTP (Perkin Elmer Life Sciences) were performed essentially as described by B. Y. Rubin (*J. Biol. Chem.* 266: 24245-24248 (1991)). Briefly, confluent monolayers of GM04663 cells in 175 cm²

TABLE 1

Sequences of the oligonucleotide primers used in RT-PCR and real-time RT-PCR analysis

| IKAP amplicon | Annealing temperature (° C.) | Primer | Sequence (5'→3') | | Position (GenBank Accession No. AK001641) |
|---|---|---|---|---|---|
| Wild-type | 57 | Forward | AGTTGTTCATCATCGAGC | (SEQ ID NO: 1) | 2459-2476 |
| | | Reverse | CATTTCCAAGAAACACCTTAGGG | (SEQ ID NO: 2) | 2607-2585 |
| Mutant | 60 | Forward | CAGGACACAAAGCTTGTATTACAGACTT | (SEQ ID NO: 3) | 2415-2438, 2513-251 |
| | | Reverse | CATTTCCAAGAAACACCTTAGGG | (SEQ ID NO: 4) | 2607-2585 |
| Total | 60 | Forward | GAGATCATCCAAGAATCGC | (SEQ ID NO: 5) | 3881-3899 |
| | | Reverse | GGTAGCTGAATTCTGCTG | (SEQ ID NO: 6) | 4160-4143 |

To control for the amount of RNA present in the samples, RT-PCR amplification of ribosomal 18S RNA was performed on all cell lysates. The use of the ribosomal 18S RNA has been shown to be an effective control for the quantity of RNA present in samples (D. Goidin, et al., "Ribosomal 18S RNA Prevails Over Glyceraldehyde-3-Phosphate Dehydrogenase and Beta-Actin Genes as Internal Standard for Quantitative Comparison of mRNA Levels in Invasive and Noninvasive Human Melanoma Cell Subpopulations", *Anal. Biochem.* 295: 17-21 (2001)). For this analysis, TaqMan Ribosomal RNA Control Reagents were used with the TaqMan EZ RT-PCR Kit (Applied Biosystems) as per the manufacturer's protocol.

Figure 2:
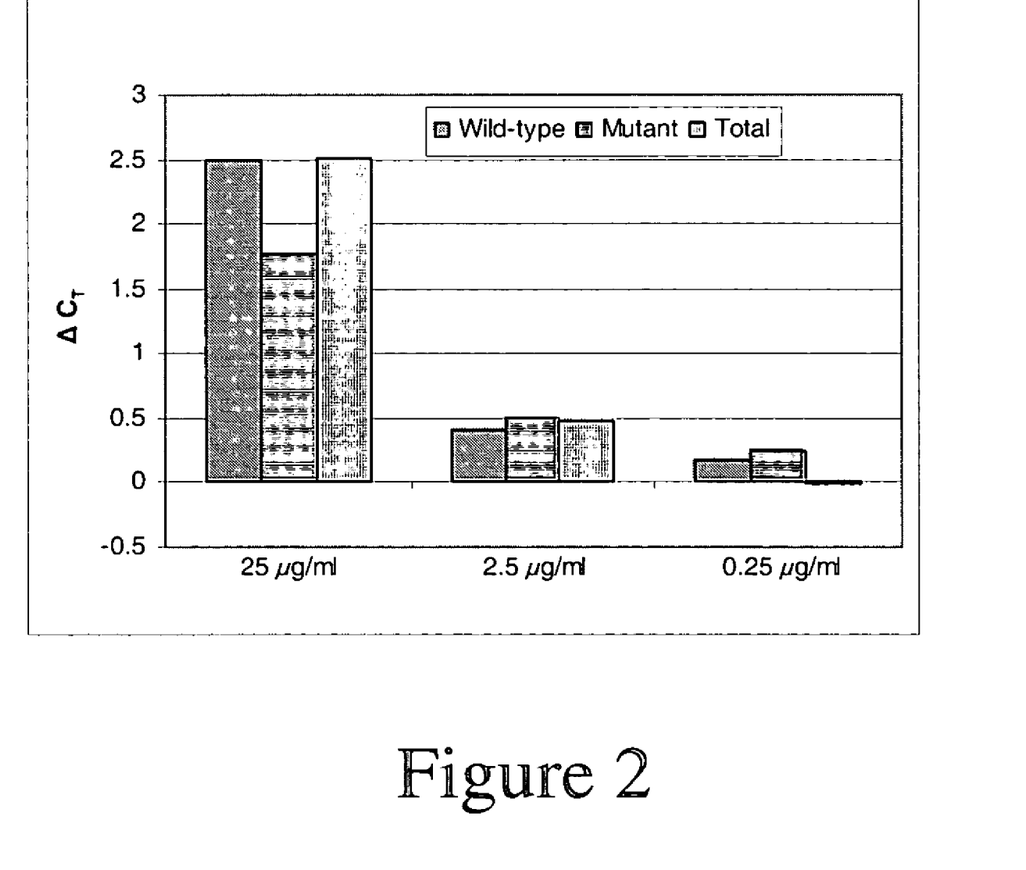

It was observed that while most of the reagents examined failed to modulate expression of IKAP transcript, δ-tocotrienol treatment mediated a concentration-dependent elevation in the level of this transcript (FIG. 2).

Figure 4:
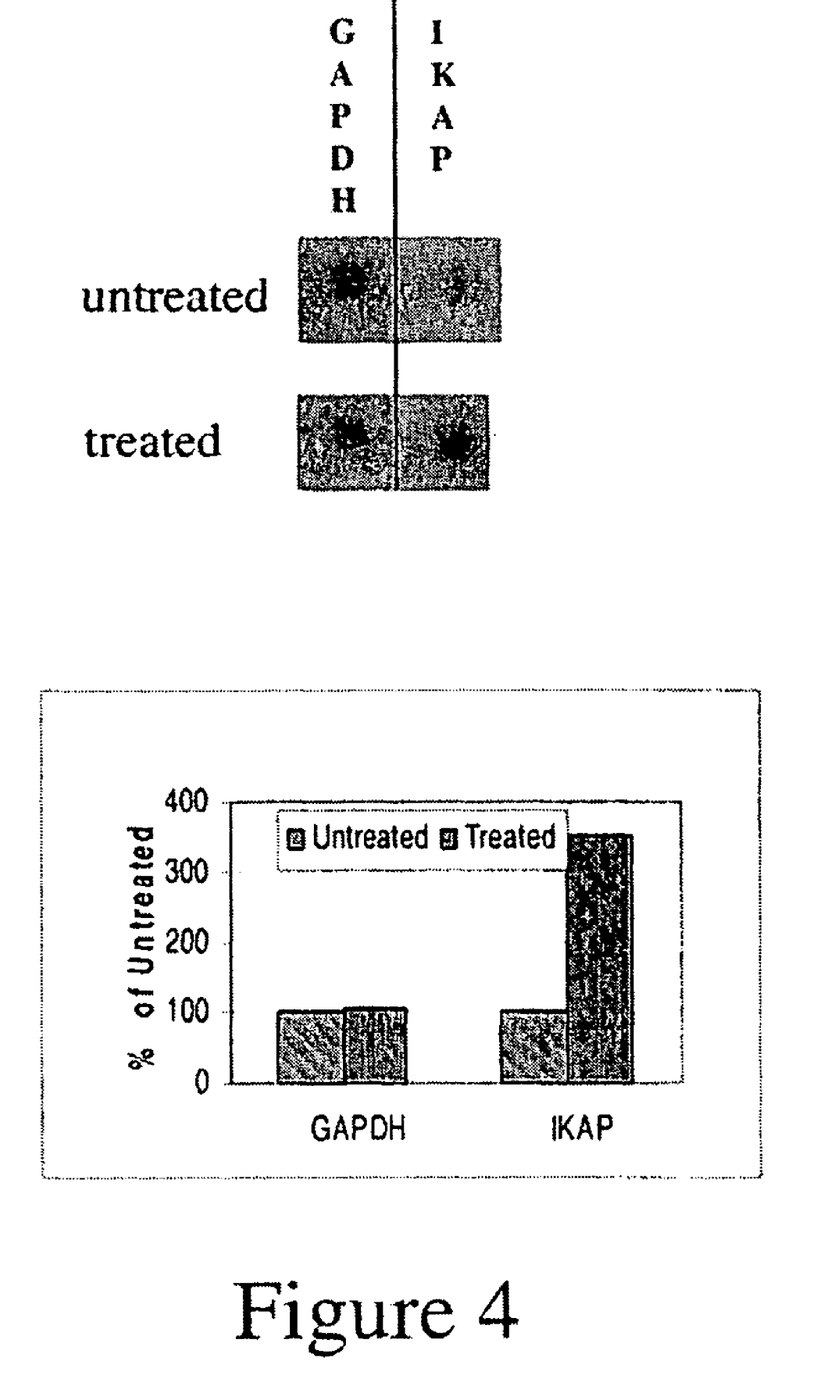

To determine whether δ-tocotrienol treatment stimulated correct splicing or elevated the cellular level of the IKAP RNA which, in turn, resulted in elevated levels of the wild-type transcript, quantitative RT-PCR was performed using primers recognizing a region of the IKAP RNA not altered by the FD-causing mutation, as well as primers which are specific for the mutant transcript. Levels of both the truncated flasks were incubated for 48 h in the presence or absence of 12.5 µg/ml 6-tocotrienol. The cells were then lysed by Dounce homogenization and the resultant nuclei were incubated with 250 µCi [$\alpha$-$^{32}$P]UTP. The radiolabeled RNA was treated with DNase, purified with Trizol LS reagent (Invitrogen), and then hybridized to 5 µg of plasmid containing either a full-length cDNA encoding IKAP or a cDNA encoding GAPDH that was immobilized on Nytran Super-Charge nylon membrane (Schleicher &Schuell) using a spot-blot apparatus. The amount of radiolabeled RNA bound was detected by autoradiography and then quantitated by densitometric scanning of the X-ray film. As can be seen in FIG. 4, δ-tocotrienol treatment resulted, in the experiment shown, in an approximately 3.5-fold increase in IKBKAP gene transcription.

EXAMPLE 3

δ-Tocotrienol Elevated the Level of the Full Length IKAP Protein

Western blot analysis was performed on cellular extracts prepared from δ-tocotrienol-treated FD-derived (GM00850 and GM04663) and normal (GM02912) fibroblast cells, using a monoclonal antibody generated against a peptide corresponding to exons 23-28 of IKAP that only recognize the full-length IKAP. Basically, cells treated for 48 h with 12.5 µg/ml of δ-tocotrienol were washed twice with PBS and lysed in 0.5 M Tris-HCl, pH 6.8, containing 1.4% SDS. Western blot analysis was performed essentially as described by B. Y. Rubin (*Proc. Natl. Acad. Sci. USA* 82: 6637-6641 (1985)). Essentially, equal amounts of protein fractionated on a 7% NuPAGE Tris-Acetate Gel (Invitrogen) were blotted onto nitrocellulose (Bio-Rad) and probed overnight with a monoclonal anti-body (BD Biosciences) directed against the carboxyl end (exons 23-28) of IKAP. The blot was then washed and probed with a goat anti-mouse antibody conjugated to alkaline phosphatase (Promega), followed by detection with Western Blue Substrate solution (Promega).

Figure 5:
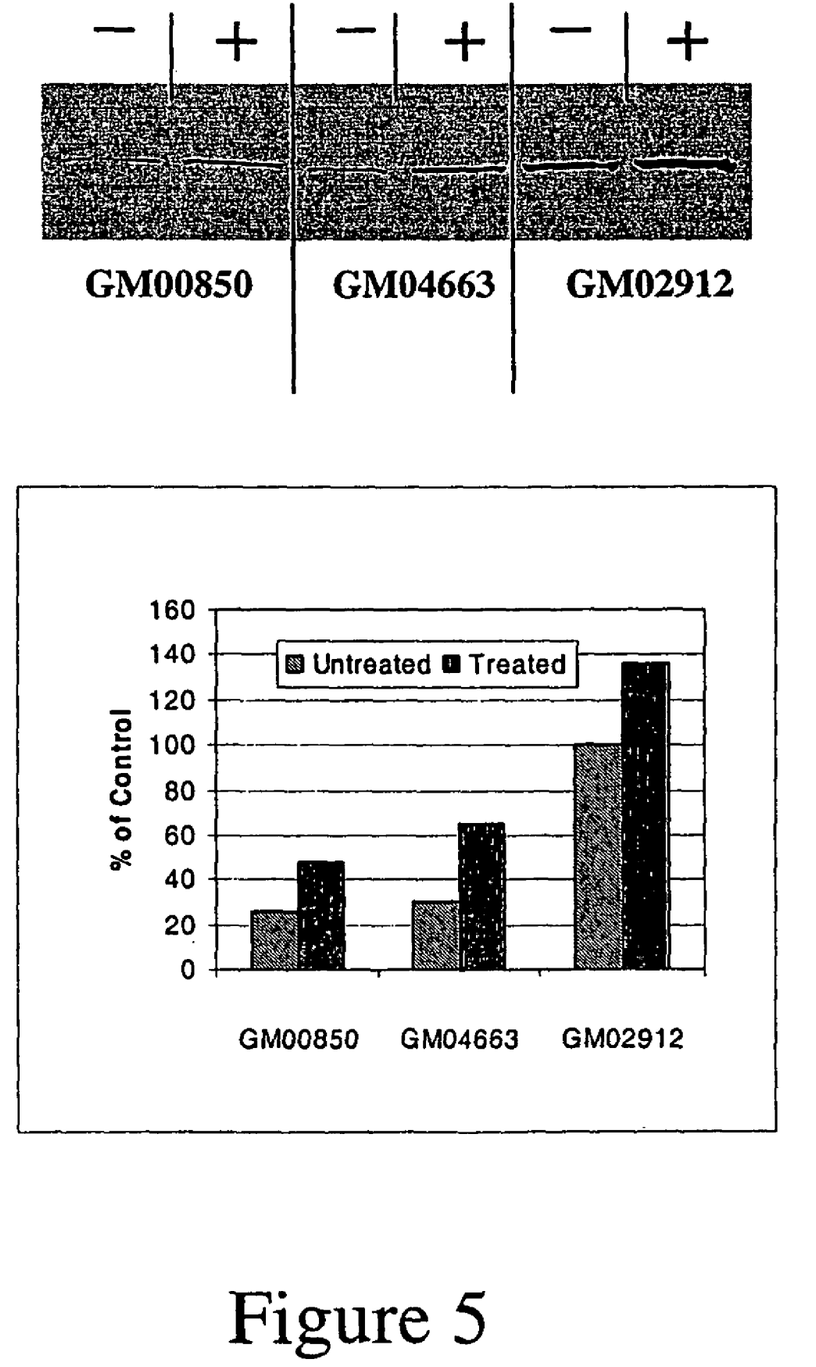

As shown in FIG. 5, δ-tocotrienol treatment resulted in an approximate two-fold increase, on average, in the amount of full-length IKAP produced in the FD-derived fibroblasts. The tocotrienol treatment of the FD-derived cells, in the experiment shown, elevated IKAP levels from 26-30% of the level present in untreated normal cells to 48-65% of the level present in these cells (FIG. 5).

EXAMPLE 4

α, β and γ Tocotrienols Elevated the Levels of the IKAP Transcripts

Figure 6:
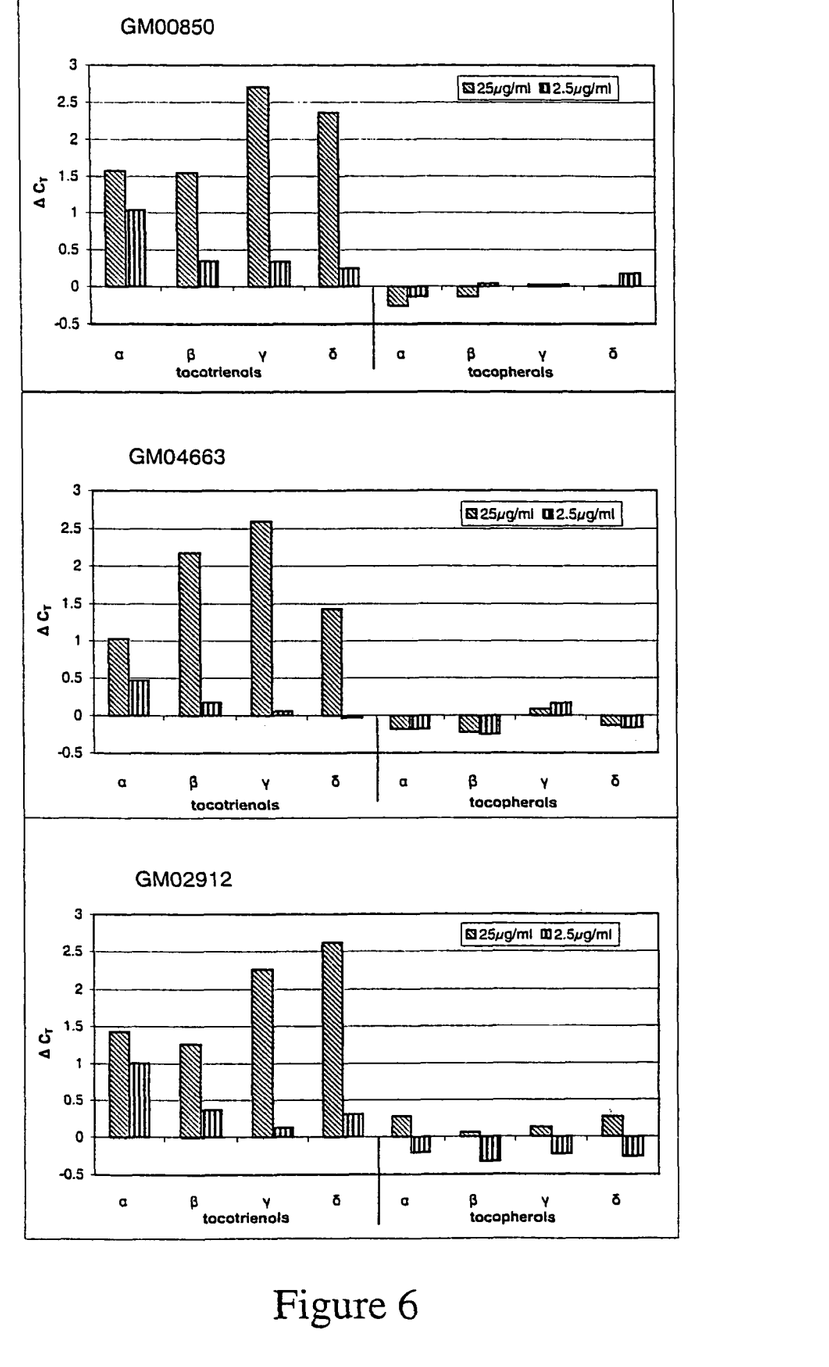
FIG. 6. Wild-type IKAP RNA levels in cells incubated in the presence of members of the vitamin E family of molecules. cDNA was prepared from GM00850, GM04663, and GM02912 cells incubated for 48 h in the absence or presence of 25 and 2.5 µg/ml of either α, β, γ or δ tocopherols or tocotrienols. The relative amounts of IKAP RNA present in these cells were determined by real-time PCR. The results presented are mean values obtained over three experiments, each done in triplicate.

To evaluate the IKAP mRNA-inducing ability of other molecules in the vitamin E family that are related to δ-tocotrienol, GM00850, GM04663, and GM02912 cells were incubated in the absence or presence of 25 and 2.5 µg/ml of either α, β, γ or δ tocopherols or tocotrienols. As can be seen in FIG. 6, treatment with all four forms of tocotrienols elevated cellular levels of the IKAP transcripts as much as sixfold, while the tocopherols had no effect on IKAP transcript levels.

Figure 7:
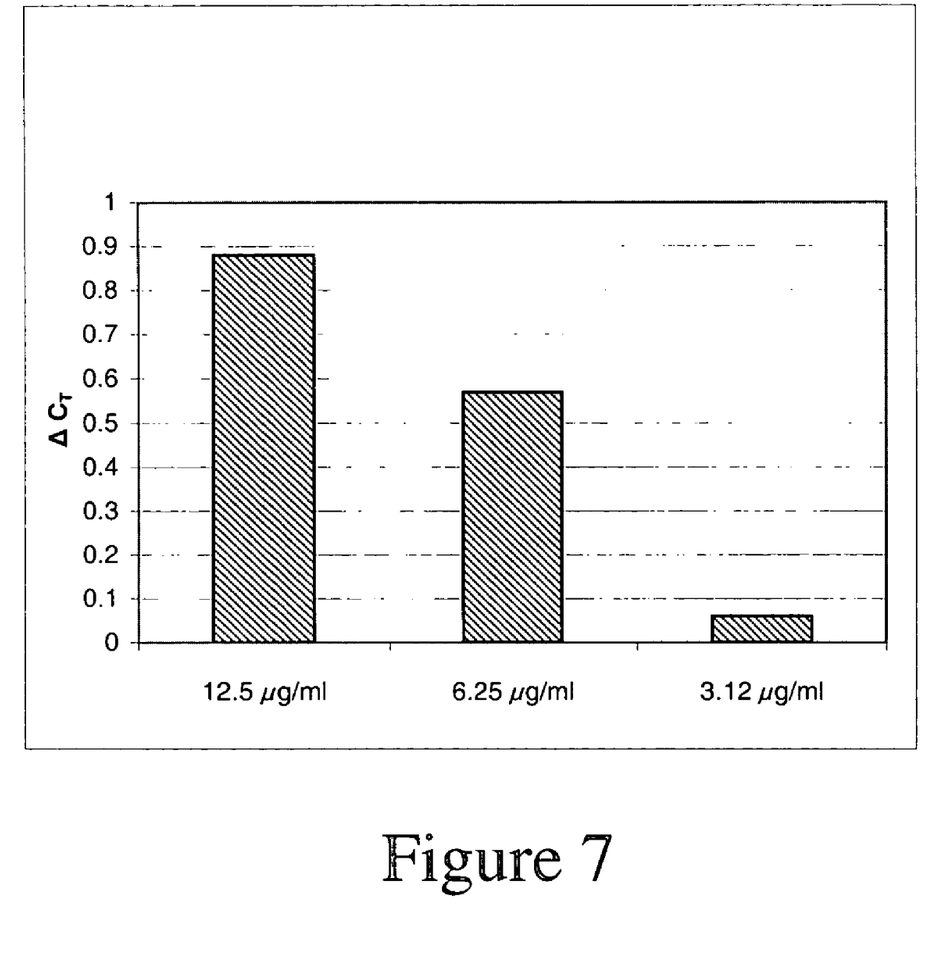
FIG. 7. Real-time RT-PCR analysis of wild-type IKAP RNA in LA1-55n cells. cDNA was prepared from LA1-55n cells incubated for 48 h in the absence or presence of varying concentrations of δ-tocotrienol. The relative amounts of IKAP RNA present in these cells were determined by real-time RT-PCR. The results presented represent mean values obtained in three experiments, each done in triplicate.

The response of the neuroblastoma-derived LA1-55n cell line, which has characteristics of sympathetic neurons (J. L. Biedler, et al., "Human Neuroblastoma Cell Differentiation, in: D. Raghavan, et al., *Principles and Practice of Genitourinary Oncology*, Lippincott-Raven, pp. 1053-1061, (1997); D. L. Lazarova, et al., "A Neuronal-Specific RNA-Binding Protein, is a Putative Regulator of N-myc pre-mRNA Processing/ Stability in Malignant Human Neuroblasts", *Oncogene* 18: 2703-2710 (1999)), to treatment with δ-tocotrienol was examined. As can be seen in FIG. 7, δ-tocotrienol induced almost a twofold increase in IKAP transcript levels in these cells.

EXAMPLE 5

Tocotrienol Supplementation in FD Patients Elevated the Level of Functional IKAP mRNA in the Patients' Blood Cells Blood samples were taken from individuals before and after the individuals began their supplementation with tocotrienols. The dosage of tocotrienols taken by the participants varied from 1 to 10 mg/kg of body weight. The level of functional IKAP mRNA present in these blood samples was determined using real time RT-PCR analysis as described above. The calculated % increase in the IKAP transcript levels was determined from the observed change in the CT. All of the results were standardized against the level of ribosomal RNA present in the samples.

Figure 8:
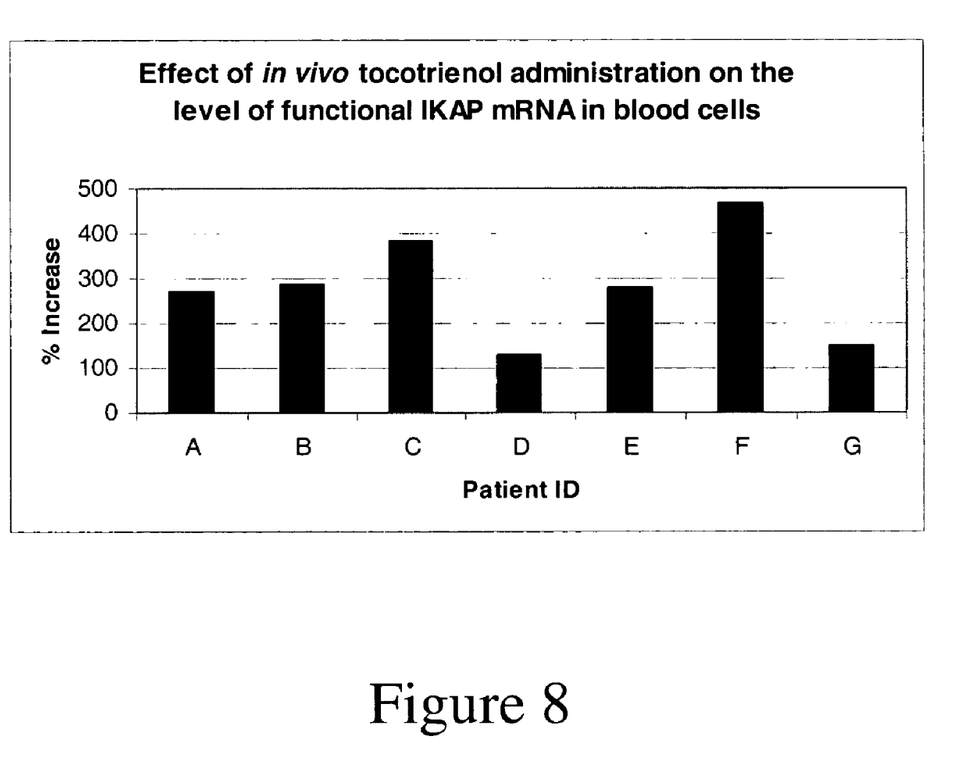
FIG. 8. Increased levels of functional IKAP mRNA in individuals with FD following supplementation with tocotrienols.

As shown in FIG. 8, in vivo supplementation with tocotrienols resulted in a clear increase in the level of functional IKAP mRNA.

EXAMPLE 6

α-Tocopherol Enhanced the Tocotrienol-Induced Elevation of IKAP mRNA Levels

Figure 9:
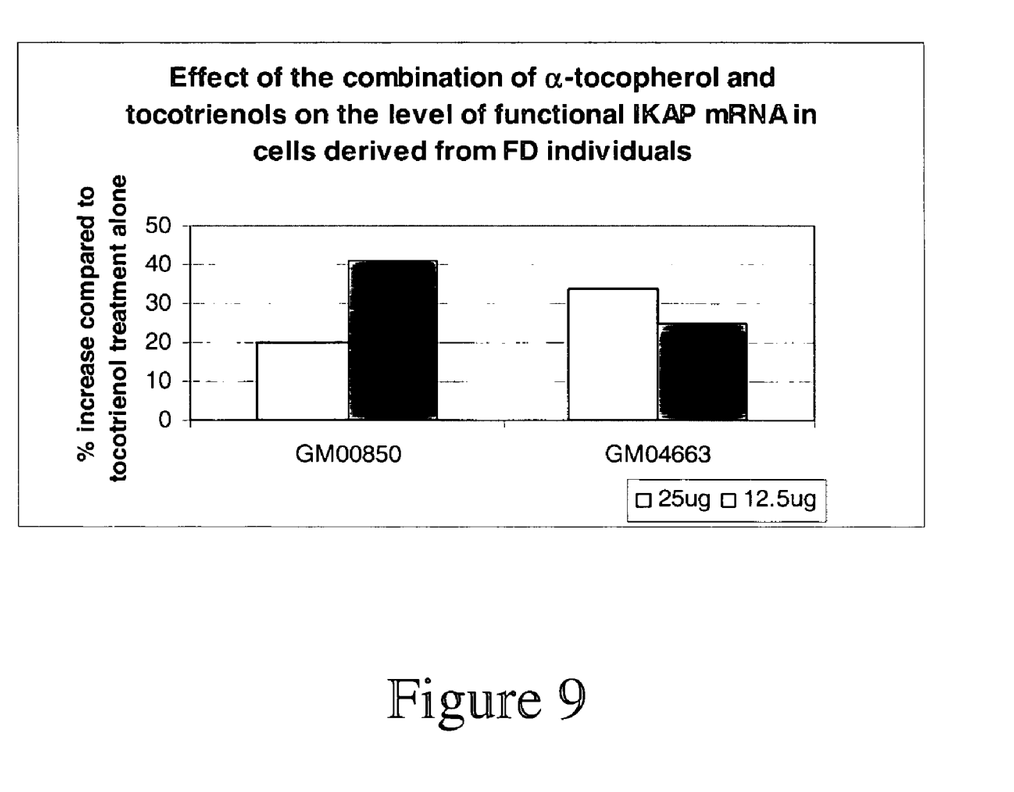
FIG. 9. α Tocopherol enhances tocotrienol-induced elevation of IKAP mRNA levels. GM00850 and GM04663 fibroblasts were treated for 48 hr with 25 or 12.5 µg/mL of a mixture of α, β, γ and δ tocotrienols+50 µg/mL α tocopherol. The % increases in IKAP mRNA levels in tocotrienol/tocopherol-treated cells as compared to tocotrienol-only treated cells, as determined by the observed changes in CT in real-time RT-PCR assays, are presented.

As described above, α, β, γ or δ tocopherol alone had no impact on IKAP mRNA levels when FD-derived or normal fibroblasts were treated for 48 hr. To determine if α-tocopherol in combination with tocotrienols would have an impact on IKAP mRNA levels, FD-derived GM00850 and GM04663 fibroblasts were treated for 48 hr with either 25 or 12.5 µg/mL of a mixture of α, β, γ and δ tocotrienols alone or in combination with 50 µg/mL of α-tocopherol. The amounts of IKAP-encoding transcripts were determined by real-time RT-PCR as described above. α-Tocopherol alone had no effect on IKAP mRNA levels, but as can be seen in FIG. 9, it enhanced the tocotrienol-induced increase in IKAP by as much as 40% as determined by the observed changes in $C_T$.

What is claimed is:

1. A method for treating an FD (Familial Dysautonomia) individual comprising providing an effective amount of a tocotrienol to said individual.

2. The method of claim 1, wherein said tocotrienol is selected from the group consisting of α, β, γ, or δ tocotrienol, or a combination thereof.

3. The method of claim 1, wherein said FD individual is of any age, from in utero throughout life.

4. The method of claim 1, wherein said tocotrienol is provided to said FD individual at 25 to 500 mg per day.

5. The method of claim 1, wherein said tocotrienol is provided to said FD individual orally, enterally or parenterally.

6. The method of claim 1, further comprising providing an effective amount of a tocopherol to said individual.

7. The method of claim 6, wherein said tocopherol is selected from the group consisting of α, β, γ, or δ tocopherol, or a combination thereof.

8. The method of claim 6, wherein said tocopherol is provided to said individual at 1 to 1000 mg per day.

* * * * *